United States Patent [19]

Wallach et al.

[11] Patent Number: 4,777,959
[45] Date of Patent: Oct. 18, 1988

[54] ARTIFACT DETECTION BASED ON HEART RATE IN A METHOD AND APPARATUS FOR INDIRECT BLOOD PRESSURE MEASUREMENT

[75] Inventors: Richard A. Wallach, Tigard; Craig H. Nelson, Hillsboro, both of Oreg.

[73] Assignee: SpaceLabs, Inc., Bothell, Wash.

[21] Appl. No.: 908,446

[22] Filed: Sep. 17, 1986

[51] Int. Cl.⁴ ............................................. A61B 5/02
[52] U.S. Cl. .................................... 128/677; 128/680; 128/672
[58] Field of Search ............... 128/677, 686, 687, 689, 128/672, 680, 681, 682, 683, 900

[56] References Cited

U.S. PATENT DOCUMENTS

4,592,365  6/1986  Georgi ................................. 128/680
4,635,645  1/1987  Fukushima ......................... 128/680

Primary Examiner—William E. Kamm
Assistant Examiner—George Manuel
Attorney, Agent, or Firm—Seed and Berry

[57] ABSTRACT

A method and apparatus for the indirect measurement of blood pressure is disclosed. Pressure is applied to a cuff attached to a patient adjacent a blood vessel and a quantity representative of the patient's blood pressure is measured as the applied pressure is changed. A first table of values of the quantity as the applied pressure is changed is formed. Values of the first table are selected as spurious high and low values in response to predetermined criteria and new values assigned to the selected values which reduces the error in calculating systolic and diastolic blood pressures from the table. A second table of heart rate values as the applied pressure is changed is formed. Selected heart rate values are set to zero based on predetermined criteria and the locations of the zeros are compared with the locations of systolic, diastolic and maximum values in first table to determine whether to reject or abort the blood pressure reading.

18 Claims, 8 Drawing Sheets

ARTIFACT DETECTION BASED ON HEART RATE IN A METHOD AND APPARATUS FOR INDIRECT BLOOD PRESSURE MEASUREMENT

BACKGROUND OF THE INVENTION

The present invention relates to blood pressure measurement, in particular to a method and apparatus for the indirect measurement of blood pressure.

In most automatic indirect methods of blood pressure measurement, a pressure cuff is attached to a patient's arm adjacent a blood vessel, the cuff is pressurized with an applied pressure which is high enough to occlude the blood vessel and the applied pressure is gradually reduced. As the pressure is reduced to below systole and then diastole, blood begins to flow through the blood vessel creating the well known Korotkoff sounds and pulsatile pressures (oscillations) in the blood vessel. The sounds can be detected by a microphone and the pressure oscillations by a pressure transducer. The sensor, whether a microphone or pressure transducer, measures a quantity which is representative of the patient's blood pressure.

A table is then formed of values of the quantity measured at various applied pressures (oscillometric values) as the applied pressure is gradually changed. Using the table the systolic and diastolic blood pressures are determined. In some blood pressure measurement systems where the applied pressure is bled down in steps, at each step the peak amplitude of the oscillations is detected. By measuring the time elapsing between successive peaks the heart rate can be calculated. A table can be formed of the calculated heart rate versus applied pressure.

In a well behaved reading of blood pressure, the oscillometric values generally increase from low values at applied pressures above the systole to a maximum value at applied pressures between systole and diastole. Similarly, the values generally increase from low values at applied pressures less than diastole to the maximum values. In some cases, however, spurious high or low values in the table can occur due to patient movement, etc., which can and often do cause erroneous determinations of systolic and diastolic blood pressures. It is desirable therefore to detect and eliminate the spurious high and low values in the table when they occur, and to use either or both of the above mentioned tables (pressure and heart rate) to reject measurements where a high level of suspected artifact is present.

SUMMARY OF THE INVENTION

The present invention provides for automatically readjusting spurious low and high values in a table of values formed from the indirect measurement of blood pressure. In the preferred embodiment the oscillometric method of blood pressure measurement is used but the invention is applicable to auscultatory blood pressure measurement as well.

The present invention also provides for comparing the location of heart rate values in the heart rate table against the location of predetermined values on the oscillometric pressure table as a method and means for rejecting blood pressure readings where high artifact content is suspected. Means are provided for setting heart rate values to zero where they exceed certain criteria. The locations of the zeros are compared with the locations of the systolic, diastolic and maximum values in the pressure table to see if the blood pressure measurement should be rejected or aborted.

DETAILED DESCRIPTION OF THE DRAWINGS

Figures 1, 3, 4:
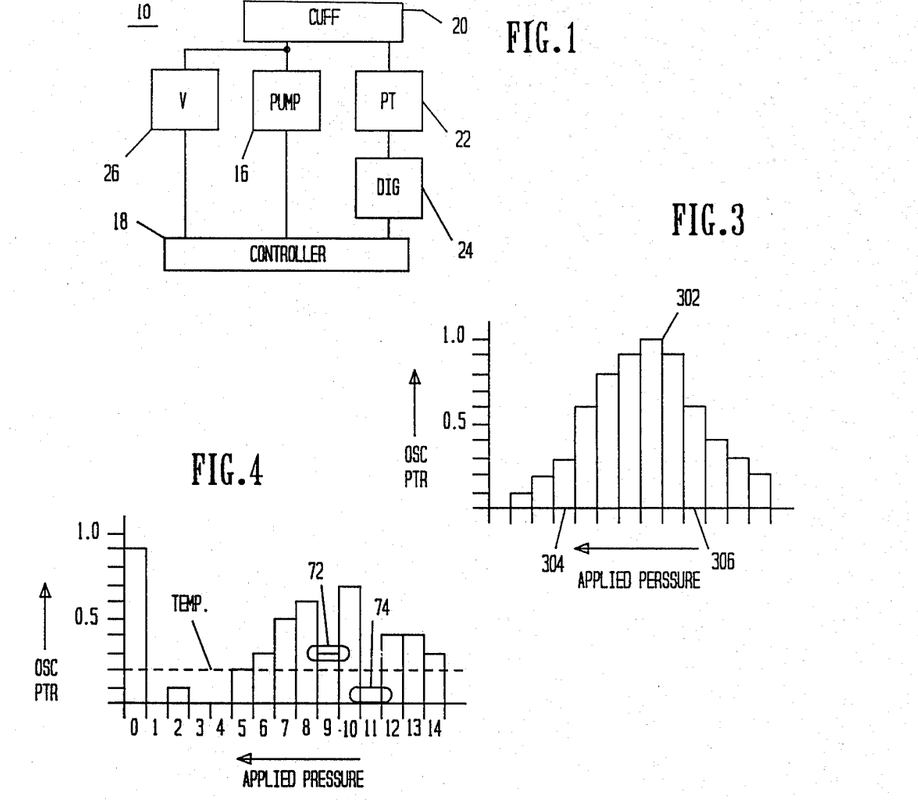
FIG. 1 is a block diagram of an apparatus for the indirect measurement of blood pressure.
FIG. 3 is a graphic representation of a table of well behaved values formed during the operation of the blood pressure measurement of FIG. 1.
FIG. 4 is a graphic representation of a table of values formed during the operation of the apparatus of FIG. 1 containing a number of spurious low values.
Figure 2:
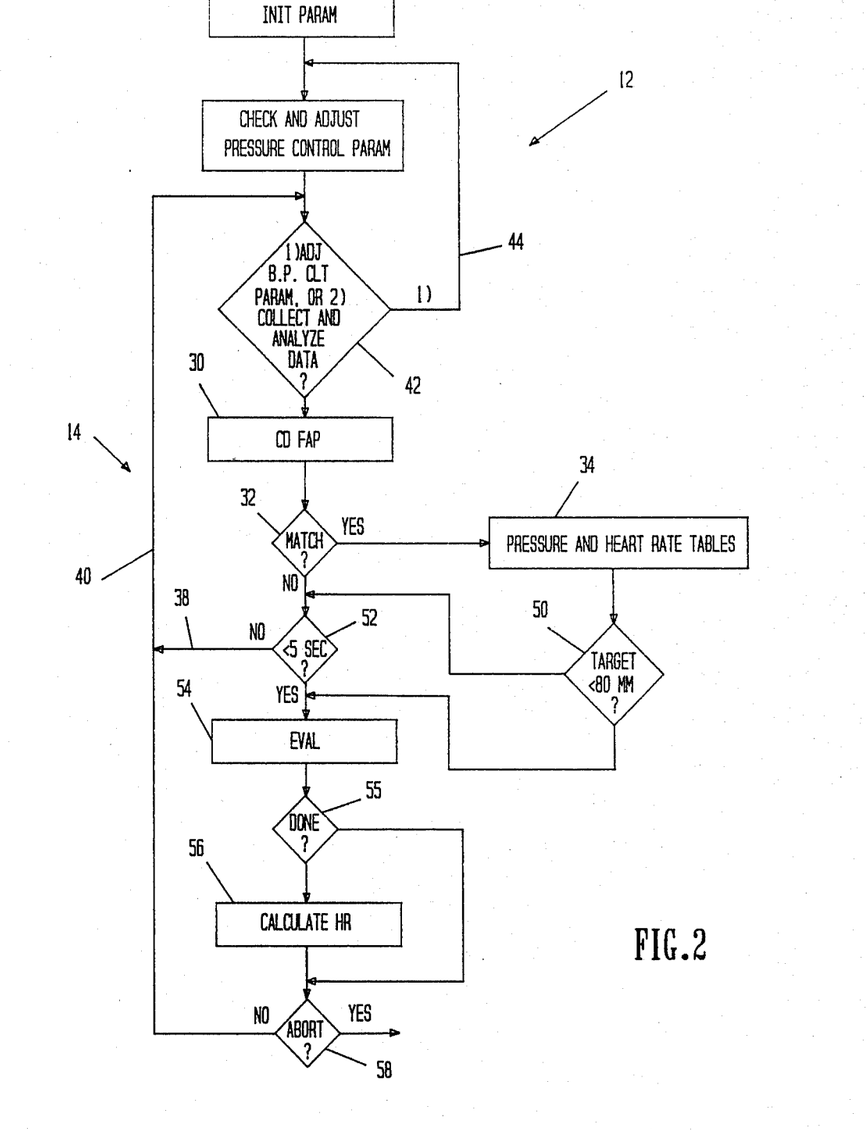
FIG. 2 is a block diagram flow chart of the overall operation of the apparatus of FIG. 1.

Referring now to the figures, the system designated generally 10 in FIG. 1 operates in basically two loops, a blood pressure control loop 12 (bp loop) and a collect and analyze data loop 14 (cd loop) in FIG. 2. Initially, a pump 16 under the control of a controller 18 in the bp loop 12 pumps up the pressure in a cuff 20 located on the patient's arm to a predetermined level, e.g. 165 millimeters (mm) of mercury. A pressure transducer 22 senses the applied pressure in the cuff and any variations due to pressure pulses in the arm's artery due to the beating of the heart. The electrical output signal from the transducer is sampled and digitized in digitizer 24 and the samples sent to the controller 18 for processing. The gain and dynamic range of the signals are checked and adjusted at this time as well. The cd loop 14 is exercised by the controller 18 on the digital data collected so far, and when completed the bp loop 12 again takes over and bleeds pressure from the cuff 20 through a valve 26 under the control of the controller 18. The pressure each time is bled down in predetermined increments, e.g., 4 or 6 or 8 mm. At each applied pressure level, the collect and analyze data lop 14 is exercised to obtain an oscillometric amplitude value representative of pulsatile pressure in the blood vessel occurring at that particular applied pressure step. FIG. 3 shows a typical bar graph showing the normalized values of the peaks of the oscillometric variations at each of the applied cuff pressure steps.

When in the collect and analyze data loop 14, the system first collects data for a peak of the oscillometric variations at a chosen applied pressure level 30. Samples of the variations are provided every millisecond and their amplitudes are checked until a peak amplitude is determined. This process takes about 150 milliseconds before a peak is formed. The peak is compared with the previous peak measured for the same applied blood pressure level. If a match occurs 32, the value of the peak is entered into an oscillometric value table 34, Within 30, the heart rate interval is measured based on the time elapsing between the successive peaks. That heart rate interval is fixed in the heart rate table if the two peaks match. If no oscillometric activity is found, zero is entered in both tables. If activity is found but the two peaks don't match, the search continues until a match occurs. This procedure helps to eliminate artifacts due to noise, patient movement, etc. Typically, a match is found in about two seconds. The system then returns to the blood pressure control loop via line 38, 40, decision box 42 and line 44 where the applied pressure is bled down one more step and the process to find and match a peak and enter the value into the table is repeated.

Eventually either the applied pressure will fall below a predetermined level 50 or the length of time for which the cuff has been pressurized will approach a predetermined interval 52. In either case this triggers the system to evaluate the table to see if a determination of systolic and diastolic pressures can be made from the table. In the preferred embodiment the predetermined applied pressure is 80 mm and the predetermined time duration of cuff pressurization is within 5 seconds of a 116 second time out criteria. If systolic and diastolic pressure calculations are unobtainable by the end of 116 seconds, the blood pressure control loop bleeds down the cuff pressure to zero.

During the evaluation phase 54, the system checks to see if there is at least three non-zero oscillometric values in the table. If there are, the highest value in the table is determined. Systolic and diastolic values are determined by looking at applied cuff pressures in the table associated with oscillometric values bearing some relationship to the maximum oscillometric value in the table e.g., systolic is the applied pressure of the first step which has an oscillometric value just below fifty percent of the maximum oscillometric value on the high applied pressure side of the maximum value while diastolic is the applied pressure of the first step just below seventy-five percent of the maximum value on the low applied pressure side of the maximum. Once EVAL determines systole and diastole (Done at 55) the system moves on to CALCULATE HR 56 where a determination based in part on heart rate is made as to whether to abort 58 the measurement. This will be described in more detail in connection with FIGS. 8 through 11.

Figure 5:
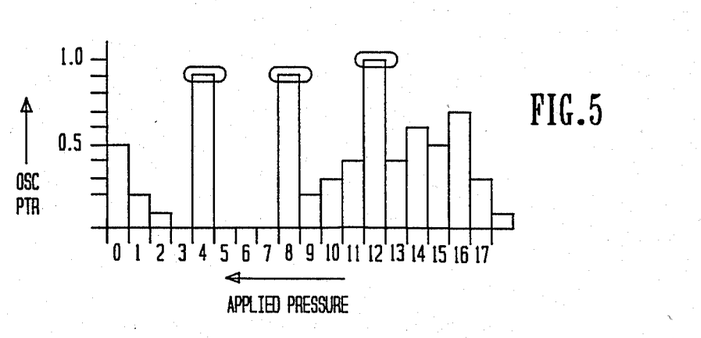
FIG. 5 is a graphic representation of a table of values formed during the operation of the apparatus of FIG. 1 containing a number of spurious high values.

FIG. 3 is a graphic representation of an ideal oscillometric table generated as described above which has a clearly defined single maximum value 302 and clearly defined systolic and diastolic pressures 304 and 306, respectively. Sometimes, however, because of sudden patient movement or patient shivering, etc., very high oscillometric table values and very low oscillometric table values can occur in the table where they are not wanted and which can cause errors when calculating the systolic and diastolic pressures as described above. See for example in FIG. 4 the spurious low values, and in FIG. 5 the spurious high values. Means are provided within EVAL 54 for fixing these lows and highs.

Figure 6:
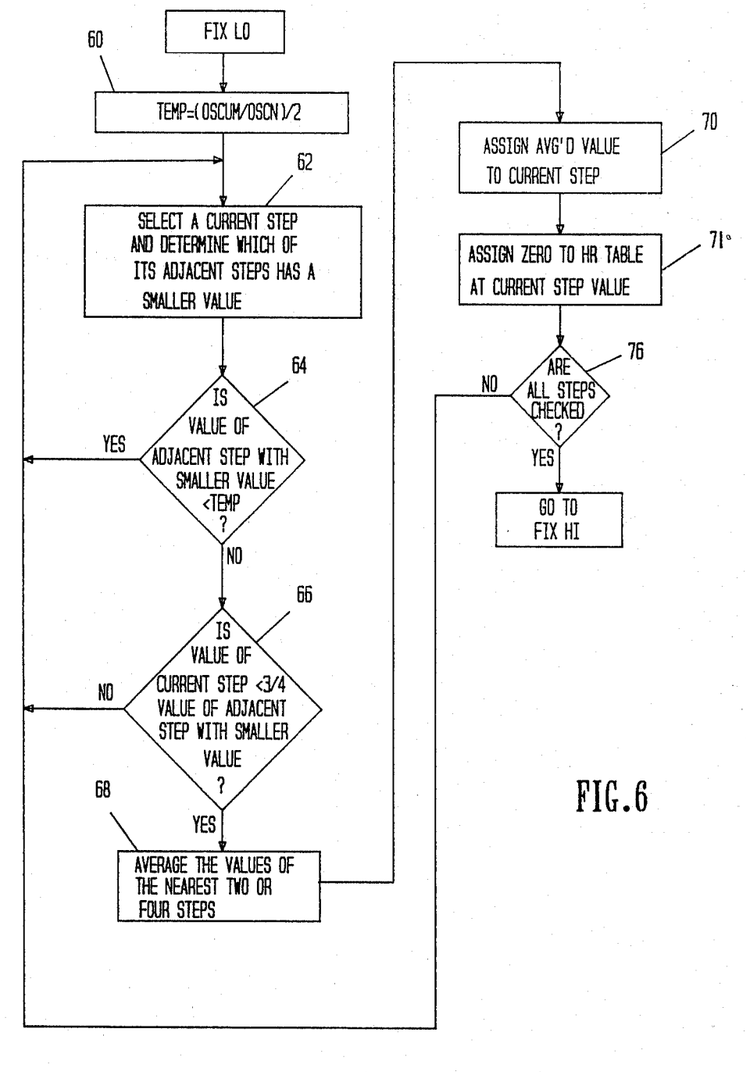
FIG. 6 is a detailed block diagram flow chart of a FIX LO portion of the EVAL portion of the block diagram of FIG. 2.

Referring now to FIG. 6, a flow chart shows how the system fixes spurious low oscillometric values in an oscillometric table such as that shown in FIG. 4. Each oscillometric table has a number of applied pressure step entries ranging from step 0 at the first step at the high applied pressure end of the table to step OSCPTR -1, the last entry at the low applied pressure end of the table. First a TEMP value equal to ½ the average value of all the non-zero oscillometric value entries in the table is calculated 60. Ignoring the zero step and the OSCPTR -1 step the system begins with step No. 1 and determines which of its adjacent steps has the smaller oscillometric value (e.g., step 0 or step 2) 62. (In the case of FIG. 4 it is step 2.) If the adjacent step with the smaller oscillometric value is less than the TEMP value then the current step being evaluated is not to be fixed 64. This is because most likely the low value occurs at a far end of the graph where it is likely not to be important.

If the value of the smaller valued adjacent step is larger than TEMP then the value of the current step is compared with ⅔ of the value of the smaller valued step 66. If the oscillometric value of the current step is smaller than this, then a decision is made to fix the value. If the current step is the second step or second to the last step then the oscillometric values of one step on each side of the current step are averaged together and the value assigned to the current step; otherwise, the values of the two steps on each side of the current step are averaged and the average value assigned to the current step in the table. The heart rate interval value for the applied pressure step in the heart rate table corresponding to the current step in the oscillometric table is set to zero. See 68, 70 and 71. In this way spurious lows are fixed. Using this method, the low values at steps 9 and 11 would be fixed indicated by the circles 72 and 74, while the values at steps 1, 3 and 4 would be left alone. When all the steps in the oscillometric table are checked for fixing the system goes on to fix the high values 76.

Figure 7:
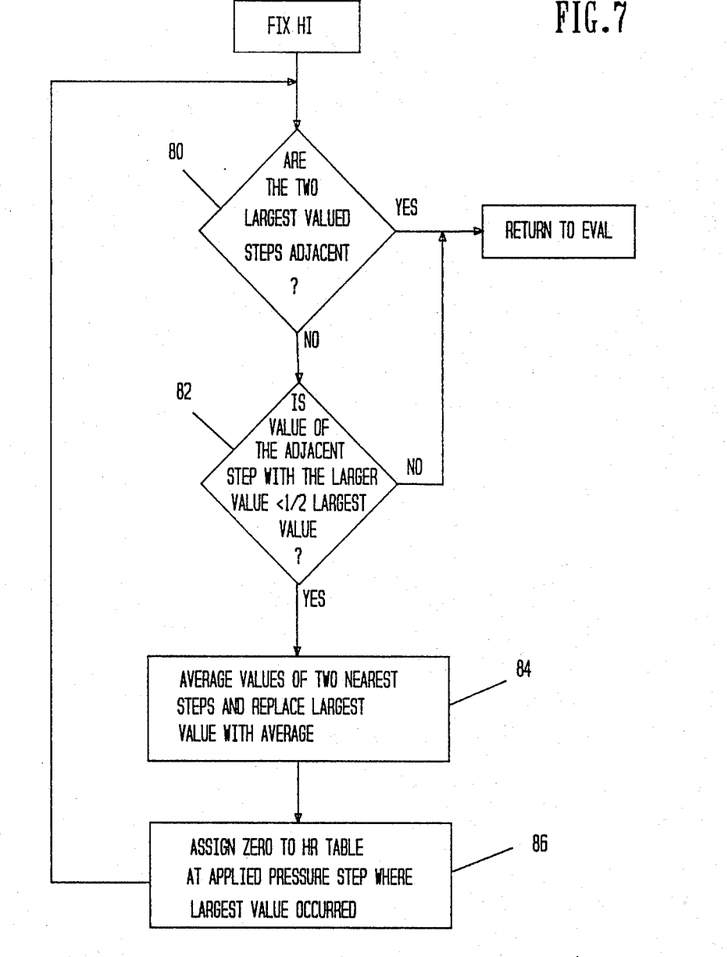
FIG. 7 is a more detailed block diagram flow chart of a FIX HI portion of the EVAL portion of the block diagram of FIG. 2.
Figure 8:
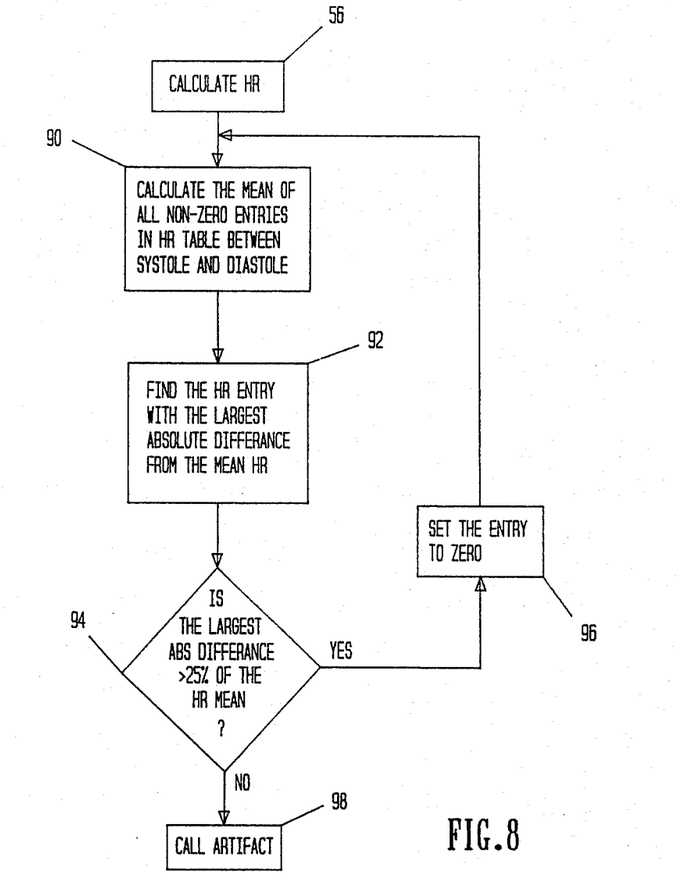
FIG. 8 is a more detailed block diagram flow chart of the CALCULATE HR portion of the block diagram of FIG. 2.

To fix the spurious highs in the table, the end samples 0 and OSCPTR -1 are ignored. The steps with the two largest oscillometric values are determined and they are checked to see how close together they are 80. For example, if they are adjacent then neither is to be considered an artifact and neither will be fixed. Where applied pressure bleed steps are small, e.g. 4 mm, the criteria for determining whether an artifact exists or not could be different, e.g., if the two largest valued steps are adjacent or only separated by one step then they are not to be considered artifacts.

If, the two steps with the largest values do not meet the above criteria then the larger valued adjacent step to the step with the largest oscillometric value is compared with one half the value of the largest valued step 82. If the value of the larger adjacent step is less than one half the largest value then the values of the steps on either side of the step with the largest value are averaged together and the average assigned to the step with the largest value 84. At the same time the corresponding heart rate value in the heart rate table is set to zero 86. If the largest peak had been adjusted, a "new" largest peak is again found and the process is repeated.

Using the above FIX HI method, the steps 4, 8 and 12 in FIG. 6 would be fixed while steps 0, 14 and 16 would be left alone.

After the FIX LO and FIX HI routines are complete the adjusted oscillometric table values are used for the determination of systolic and diastolic pressures within EVAL. If no systolic has been determined, the blood pressure control loop first deflates the cuff. Then after a patient safety period has expired, the cuff is pumped to an applied pressure larger than before since it is assumed that the previous highest applied pressure wasn't high enough to measure systolic as described earlier. If diastole is not found, then the collect data and analyze loop and EVAL routine are repeated until a diastolic pressure is determined or until the applied pressure drops to 20 mm or until the safety timer times out.

In the preferred embodiment the FIX LO routine is performed before the FIX HI routine, otherwise normal values might be treated as spurious high values if the normal values are adjacent spurious low values. When spurious low values are fixed first, the TEMP criteria 64 prevents the system from elevating normal low values next to a spurious high value.

Once a systolic and diastolic pressure has been obtained and the done flag 55 is set the system moves on from EVAL 54 to the calculate heart rate routine 56. This is shown in more detail in FIG. 8. First, the mean value of all the non-zero entries in the heart rate table occurring between the applied pressure steps for systole and diastole as determined by EVAL is calculated 90. Then the heart rate entry with the largest absolute difference from the mean heart rate is determined 92. If this value is greater then 25% of the heart rate mean value 94 then the above mentioned entry is set to zero in the heart rate table (see 96) and the process is repeated until no entry in table is found whose absolute difference from the mean is greater than 25%. When this occurs subroutine Artifact 98 is called.

Figure 9:
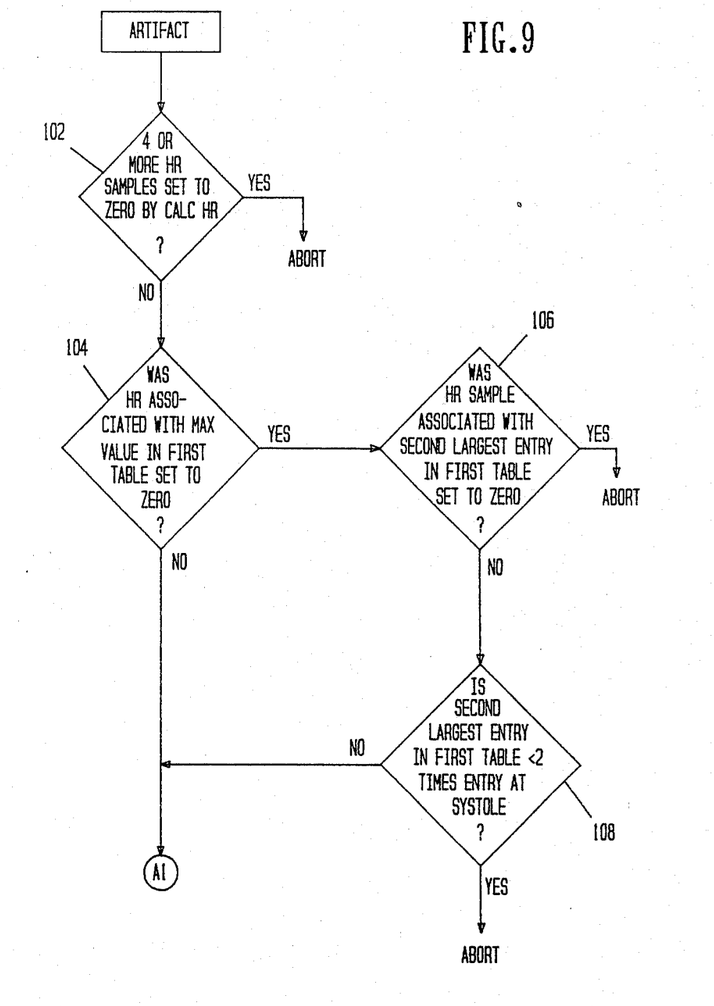
FIG. 9 is a detailed block diagram of a first portion of the ARTIFACT subroutine called for by the CALCULATE HR portion of FIG. 8.
Figure 10:
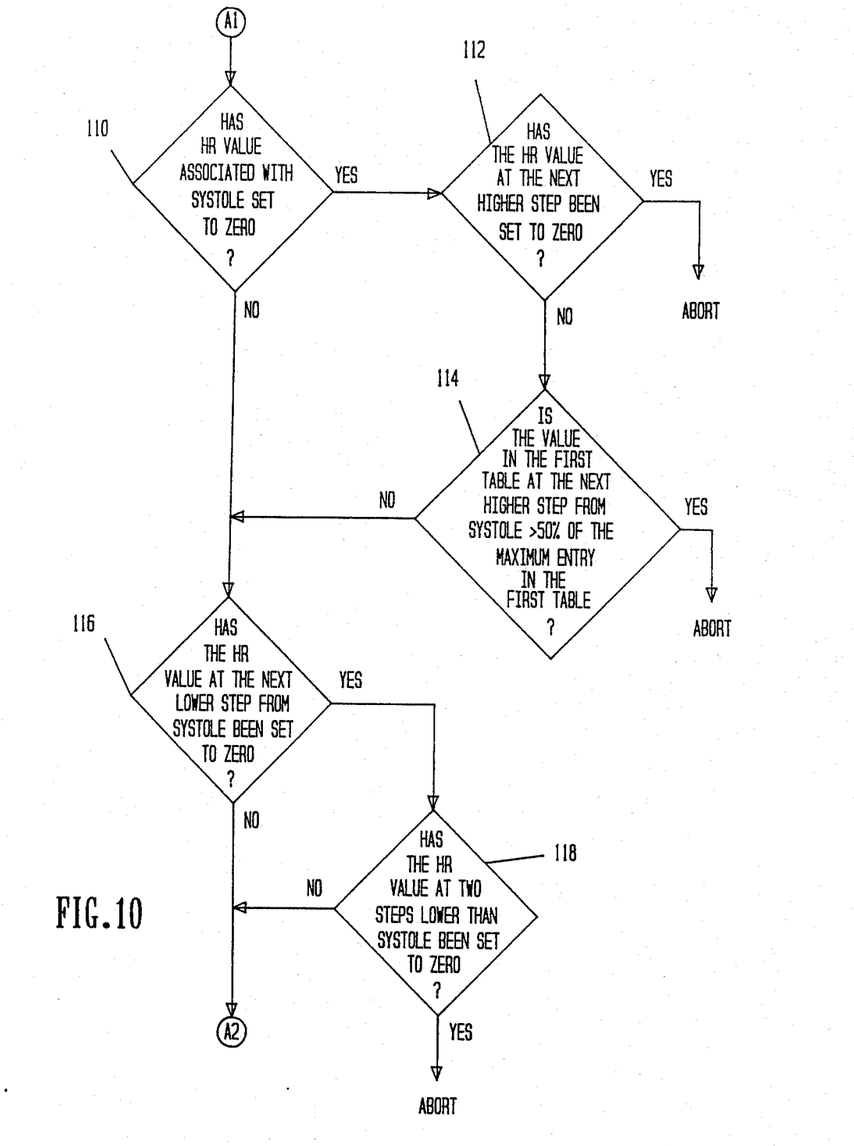
FIG. 10 is a detailed block diagram of a second portion of ARTIFACT.
Figure 11:
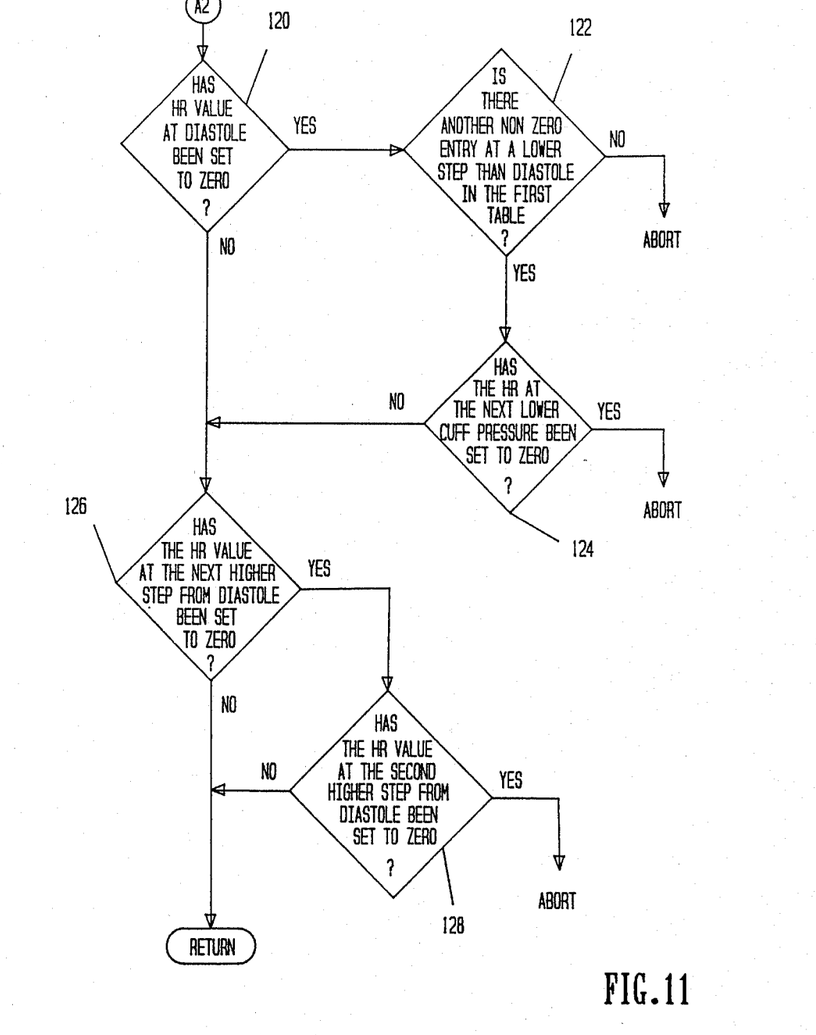
FIG. 11 is a detailed block diagram of a third portion of ARTIFACT.

The subroutine Artifact is shown in FIGS. 9 through 11. In FIG. 9, if four or more heart rate values in heart rate table were set to zero by the calculate heart rate routine 56 then the current blood pressure measurement is aborted 102. Otherwise, the heart rate table is compared with oscillometric table to determine if the heart rate value associated with the maximum oscillometric value in the oscillometric table was set to zero 104. (For purposes of the remainder of the description of FIGS. 9 through 11 setting to zero includes any heart rate set to zero from CALCULATE HR, FIX, HI, FIX LO, or CDFAP 30.) If the heart rate value associated with the maximum oscillometric entry in oscillometric table was set to zero then the tables are compared again to determine if the heart rate value associated with the second largest oscillometric value in the oscillometric table was set to zero 10. If it was the measurement is aborted; if not, the second largest value in the oscillometric table is examined to determine if it is less than two times the oscillometric value located at the systolic pressure step 108. If it is, the measurement is aborted.

If the heart rate value associated with the maximum value in the oscillometric table was not set to zero, or if it was, but the second largest value is non zero and greater than two times the oscillometric value at systole, then the measurement is not aborted at this point.

The above discussion relating to a method and means for aborting the blood pressure measurement are based on an evaluation that the heart rate measurements around the applied pressure step location of the maximum oscillation value are anomalous. In FIGS. 10 and 11 a similar method and means is provided for the step locations around the systolic and diastolic pressures.

Referring now to FIG. 10, the heart rate and oscillometric tables are compared to determine whether the heart rate value associated with the systolic pressure step had been set to zero 110. If it was then the heart rate table is examined to determine if the heart rate value at the next higher applied pressure step was set to zero 112. If it was, then the measurement is aborted; if not, the oscillometric value at one step above systole is examined to determine if it is greater than 50% of the maximum oscillometric value in the oscillometric table, see 114. If it is then the measurement is aborted.

If the heart rate value associated with the systolic pressure step was not set to zero or the oscillometric value at one step above systole is non-zero and less than or equal to 50% of the maximum value in the oscillometric table then the heart rate sample at the next step lower than systole is examined 116. If it is zero then the heart rate at two applied pressure steps lower than systolic is examined 118. If the heart rate there is zero then the measurement is aborted.

If the heart rate value at the applied pressure step lower, but next to, systole is non-zero or if it is zero but the heart rate value at two steps less then systole is non-zero then the measurement is not aborted at this point.

Referring now to FIG. 11, the tables are compared and if the heart rate associated with diastolic applied pressure was set to zero 120 then the table is examined to determine if there is a non-zero oscillometric value at a lower applied pressure step than diastolic in the oscillometric table, see 122. If there is and the heart rate value at the next lower pressure step was set to zero 124 then the measurement is aborted. If the heart rate value associated with diastole is non-zero, or if it is zero and there is no oscillometric value at the lower step or if the outcome of 124 is no then the heart rate table is examined to see if the heart rate at the next higher step from diastole is zero 126. If it is then the heart rate table is examined again to see if the heart rate value at the second step above diastole was set to zero 128. If it was the measurement is abandoned. If the heart rate value at the next higher step from diastole was non-zero, or if it was zero but the heart rate value at the second higher step was non-zero then the blood pressure measurement is treated as valid.

What is claimed is:

1. An apparatus for the measurement of blood pressure comprising:
   a pressure cuff attachable to a patient adjacent a blood vessel;
   means for changing pressure in the cuff to apply pressure to the patient;
   means communicating with the cuff for measuring a quantity representative of the patient's blood pressure;
   means for forming a first table of values attained by said quantity as the applied pressure is changed;
   means for determining a blood pressure reading of said patient from said first table;
   means for forming a second table of heart rate values of said patient, including zero values, as the applied pressure is changed;
   means for setting selected heart rate values to zero in said second table in response to predetermined criteria; and
   means for rejecting said blood pressure reading when the location of said zero heart rate values in said second table correspond with the location of predetermined values in said first table.

2. The apparatus of claim 1 wherein said blood pressure measurement includes means for determining systolic and diastolic blood pressure.

3. The apparatus of claim 2 wherein said zero setting means comprises means for determining the mean of all non-zero heart rate values occurring between the systolic and diastolic blood pressure readings and comparing the heart rate values in said second table with said mean to determine which are to be set to zero.

4. The apparatus of claim 3 wherein said apparatus further comprises:
   means for adjusting the values of spurious low and high values occurring in the first table; and
   said setting means comprises means for setting the heart rate values corresponding to said adjusted values in said first table to zero in said second table.

5. The apparatus of claim 2 wherein the location of said predetermined values in said first table comprises locations associated with a maximum value, the systolic value and the diastolic value in said first table.

6. A method for the measurement of blood pressure comprising the steps of:
   attaching a blood pressure cuff to a patient adjacent a blood vessel;
   changing the pressure in the cuff to apply pressure to the patient;
   providing communication with the cuff for measuring a quantity representative of the patient's blood pressure:
   forming a first table of values attained by said quantity as the applied pressure is changed;
   determining a blood pressure reading of said patient from said first table;
   forming a second table of heart rate values of said patient, including zero values, as the applied pressure is changed;
   setting selected heart rate values to zero in said second table;
   rejecting said blood pressure reading when the location of said zero heart rate values in said second table corresponds with the location of predetermined values in said first table.

7. The method of claim 6 wherein said step of determining said blood pressure reading comprises determining systolic and diastolic blood pressure.

8. The method of claim 7 wherein the step of setting selected heart rate values to zero comprises the steps of:
   forming the mean of all non-zero heat rate values in the second table occurring between systolic and diastolic; and
   comparing the non-zero heart rate values with the mean to determine in accordance with predetermined criteria which heart rate values shall be set to zero.

9. The method of claim 8 wherein said predetermined criteria comprises setting the heart rate which has the largest absolute difference from the mean to zero if the absolute value of the difference between the heart rate value which has the largest absolute difference from the mean and the mean is greater than twenty-five percent.

10. The method of claim 6 wherein said rejecting step comprises:
   rejecting said blood pressure reading when the heart rate values corresponding to both the first and second largest values in the first table are zero.

11. The method of claim 7 wherein said rejecting step comprises:
   rejecting said blood pressure reading when the heart rate value corresponding to the largest value in the first table is zero, the heart rate corresponding to the second largest value in the first table is non-zero but the second largest value is less than or equal to two times the value in the first table located at the systolic pressure step.

12. The method of claim 8 wherein said method further comprises:
   adjusting the values of spurious low and high values occurring in the first table; and
   setting corresponding heart rate values to zero in said second table.

13. The method of claim 7 wherein said rejecting step comprises:
   rejecting the blood pressure reading when the heart rate value associated with the systolic blood pressure in the first table is zero and the heart rate value associated with the value in the first table at the next higher applied pressure step from systolic is zero.

14. The method of claim 8 wherein said method further comprises the step of rejecting said blood pressure reading when four or more heart rate values are set to zero by said setting step.

15. The method of claim 7 wherein said rejecting step comprises:
   rejecting said blood pressure reading when the heart rate value associated with the systolic pressure in the first table is zero, the heart rate value at the next higher applied pressure step in the first table is non-zero, but the associated value in the first table for the next higher applied pressure step is greater than fifty percent of the maximum value in the first table.

16. The method of claim 7 wherein said rejecting step comprises:
   rejecting said blood pressure reading when the heart rate value associated with systole is non-zero but the heart rate value associated with the next two lower steps are both zero.

17. The method of claim 7 wherein said rejecting step comprises:
   rejecting said blood pressure reading when (i) the heart rate associated with diastolic is zero, and (ii) a non-zero entry exists in the first table at a step lower than diastolic and (iii) the heart rate associated with the next lower step from the non-zero entry is zero.

18. The method of claim 7 wherein said rejecting step comprises:
   rejecting said blood pressure when (i) the heart rate associated with diastole is non-zero, or the heart rate associated with diastolic is zero and there is an entry in the first table at a lower step but the heart rate at the next lower step is non-zero and (ii) the heart rate associated with the next two higher steps from diastolic are both zero.

* * * * *

UNITED STATES PATENT AND TRADEMARK OFFICE
CERTIFICATE OF CORRECTION

PATENT NO. : 4,777,959

DATED : October 18, 1988

INVENTOR(S) : Richard A. Wallach; Craig H. Nelson

It is certified that error appears in the above-identified patent and that said Letters Patent is hereby corrected as shown below:

In claim 8, column 7, line 49, delete "heat" and substitute therefor --heart--.

Signed and Sealed this

Second Day of May, 1989

Attest:

DONALD J. QUIGG

*Attesting Officer*  *Commissioner of Patents and Trademarks*